(12) United States Patent
Feith et al.

(10) Patent No.: US 9,375,559 B2
(45) Date of Patent: Jun. 28, 2016

(54) MULTI-VALVE INJECTION/ASPIRATION MANIFOLD WITH NEEDLELESS ACCESS CONNECTION

(71) Applicant: CareFusion 303, Inc., San Diego, CA (US)

(72) Inventors: Raymond P. Feith, Chino Hills, CA (US); Tim Truitt, Orange, CA (US); Gary S. Werschmidt, Yorba Linda, CA (US)

(73) Assignee: CareFusion 303, Inc., San Diego, CA (US)

( * ) Notice: Subject to any disclaimer, the term of this patent is extended or adjusted under 35 U.S.C. 154(b) by 88 days.

(21) Appl. No.: 14/300,160

(22) Filed: Jun. 9, 2014

(65) Prior Publication Data

US 2014/0288512 A1    Sep. 25, 2014

Related U.S. Application Data

(60) Continuation of application No. 13/564,669, filed on Aug. 1, 2012, now Pat. No. 8,747,370, which is a continuation of application No. 10/816,183, filed on Mar. 31, 2004, now Pat. No. 8,257,320, which is a division of application No. 10/113,087, filed on Apr. 1, 2002, now abandoned, which is a continuation-in-part of application No. 09/154,939, filed on Sep. 17, 1998, now Pat. No. 6,364,861.

(51) Int. Cl.
| | |
|---|---|
| *A61M 39/02* | (2006.01) |
| *A61M 39/24* | (2006.01) |
| *A61M 39/22* | (2006.01) |
| *A61M 5/14* | (2006.01) |

(52) U.S. Cl.
CPC ............ *A61M 39/22* (2013.01); *A61M 5/1408* (2013.01); *A61M 39/02* (2013.01); *A61M 39/24* (2013.01); *A61M 2039/0202* (2013.01); *A61M 2039/242* (2013.01); *A61M 2039/246* (2013.01); *A61M 2039/2433* (2013.01); *A61M 2039/2466* (2013.01); *Y10T 137/7843* (2015.04)

(58) Field of Classification Search
CPC ............... A61M 2039/242; A61M 2039/2433; A61M 2039/2446; A61M 2039/246; A61M 2039/2466; A61M 39/02; A61M 39/22; A61M 39/24; A61M 39/225; A61M 5/1408; Y10T 137/7843

See application file for complete search history.

(56) References Cited

U.S. PATENT DOCUMENTS

| | | | |
|---|---|---|---|
| 3,889,710 | A | 6/1975 | Brost |
| 3,954,121 | A | 5/1976 | Kardos |
| 4,141,379 | A | 2/1979 | Manske |
| 4,222,407 | A | 9/1980 | Ruschke et al. |
| 4,246,932 | A * | 1/1981 | Raines .............. A61M 5/31 137/512 |
| 4,369,812 | A | 1/1983 | Paradis et al. |
| 4,506,691 | A * | 3/1985 | Tseo .............. A61M 39/02 137/1 |
| 4,556,086 | A | 12/1985 | Raines |
| 4,666,429 | A * | 5/1987 | Stone .............. A61M 5/1408 137/605 |

(Continued)

*Primary Examiner* — Quynh-Nhu H Vu

(74) *Attorney, Agent, or Firm* — McDermott Will & Emery LLP

(57) ABSTRACT

An IV manifold includes a plurality of injection/aspiration ports including a needleless access port (NAC). A check valve included in the manifold is generally located between injection ports. A two-way aspiration can be provided by the NAC having a single elongate valve element including a plug at one end. The elongate valve element has properties for resiliently and sealingly biasing the plug into an aperture of the NAC. In use, the plug is mechanically displaced by insertion of a male Luer for injection or aspiration.

18 Claims, 17 Drawing Sheets

(56) References Cited

U.S. PATENT DOCUMENTS

| | | | |
|---|---|---|---|
| 4,729,401 A * | 3/1988 | Raines | A61M 39/24 137/512 |
| 4,908,018 A * | 3/1990 | Thomsen | A61M 5/1408 137/903 |
| 4,915,688 A * | 4/1990 | Bischof et al. | 604/83 |
| 4,922,954 A | 5/1990 | Blomquist et al. | |
| 4,946,448 A | 8/1990 | Richmond | |
| 5,020,562 A | 6/1991 | Richmond et al. | |
| 5,190,525 A * | 3/1993 | Oswald | A61M 39/02 604/83 |
| 5,192,269 A | 3/1993 | Poli et al. | |
| 5,205,834 A | 4/1993 | Moorehead et al. | |
| 5,356,375 A * | 10/1994 | Higley | A61M 5/36 604/142 |
| 5,360,413 A | 11/1994 | Leason et al. | |
| 5,431,185 A | 7/1995 | Shannon et al. | |
| 5,549,577 A | 8/1996 | Siegel et al. | |
| 5,573,516 A | 11/1996 | Tyner | |
| 5,697,904 A * | 12/1997 | Raines et al. | 604/82 |
| 5,738,662 A * | 4/1998 | Shannon | A61M 5/1408 137/606 |
| 5,810,768 A * | 9/1998 | Lopez | A61M 39/02 600/573 |
| 6,364,861 B1 | 4/2002 | Feith et al. | |

\* cited by examiner

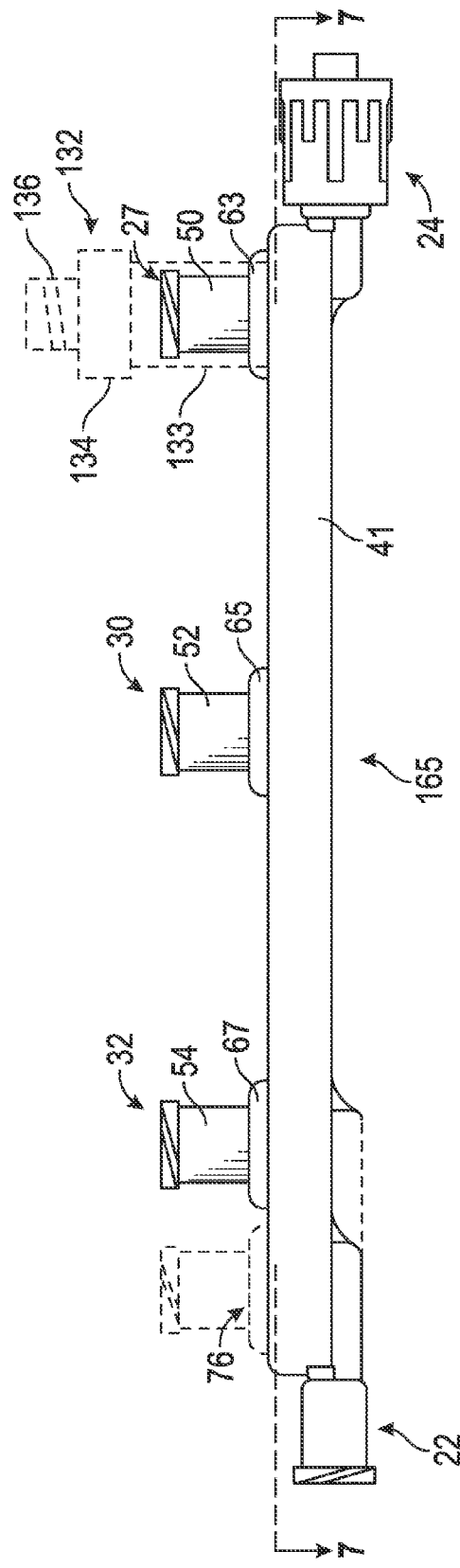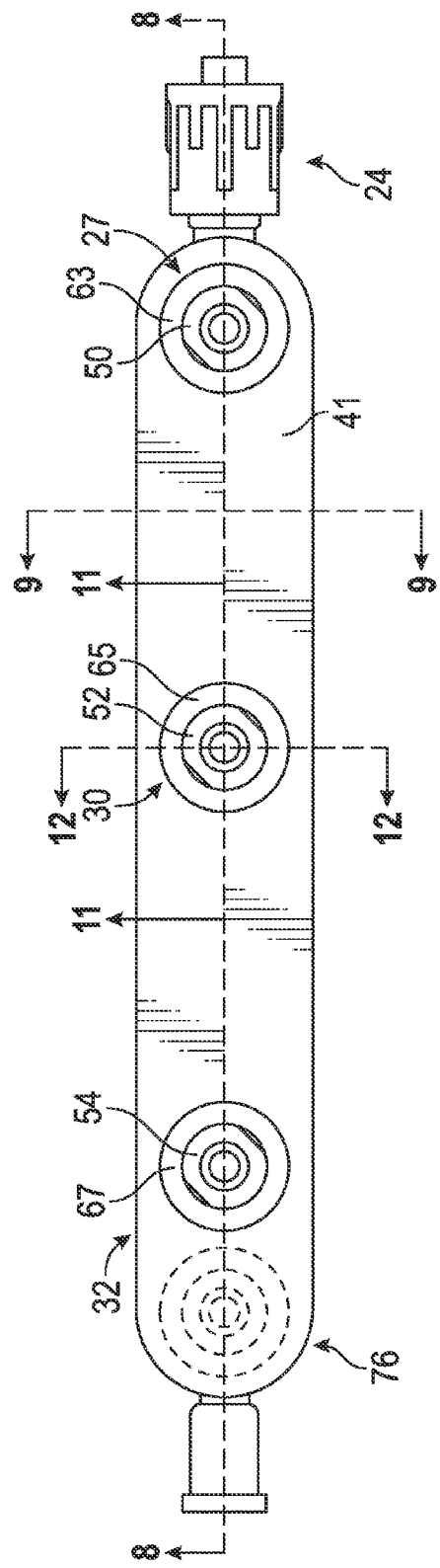
FIG. 5
FIG. 6

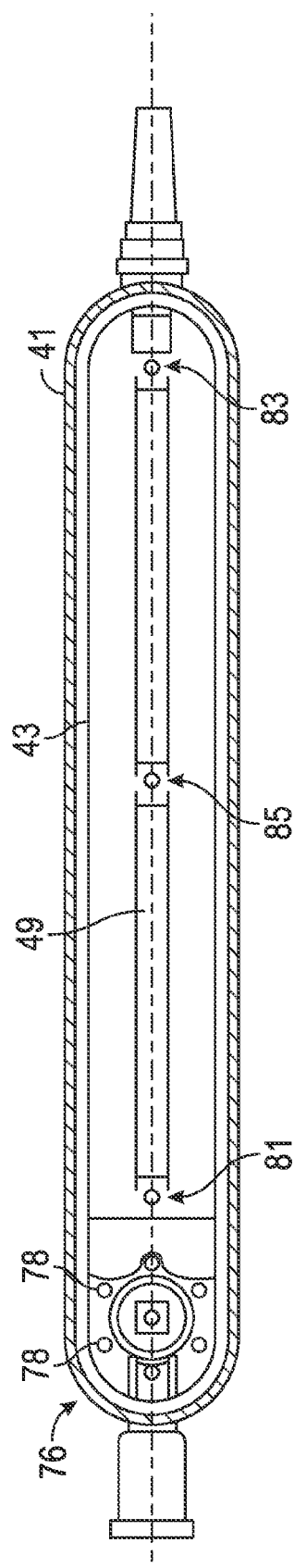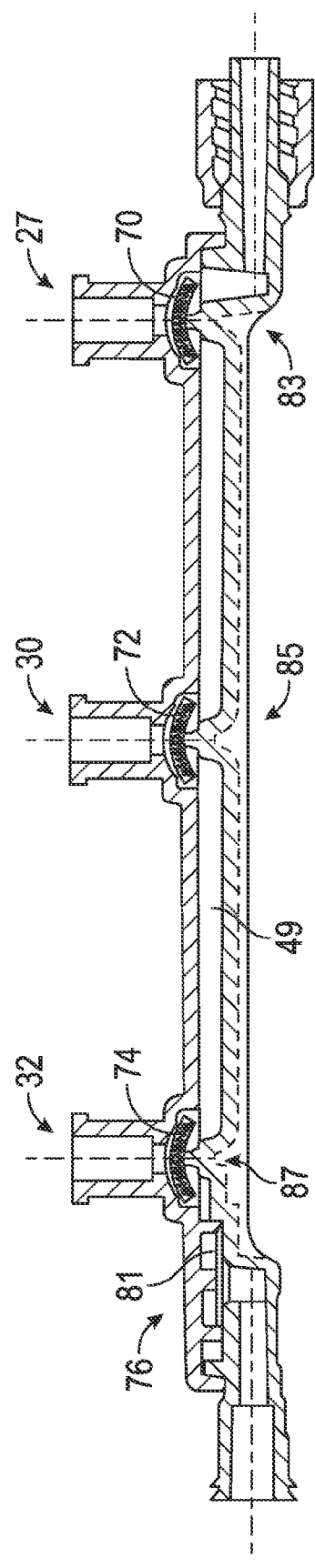

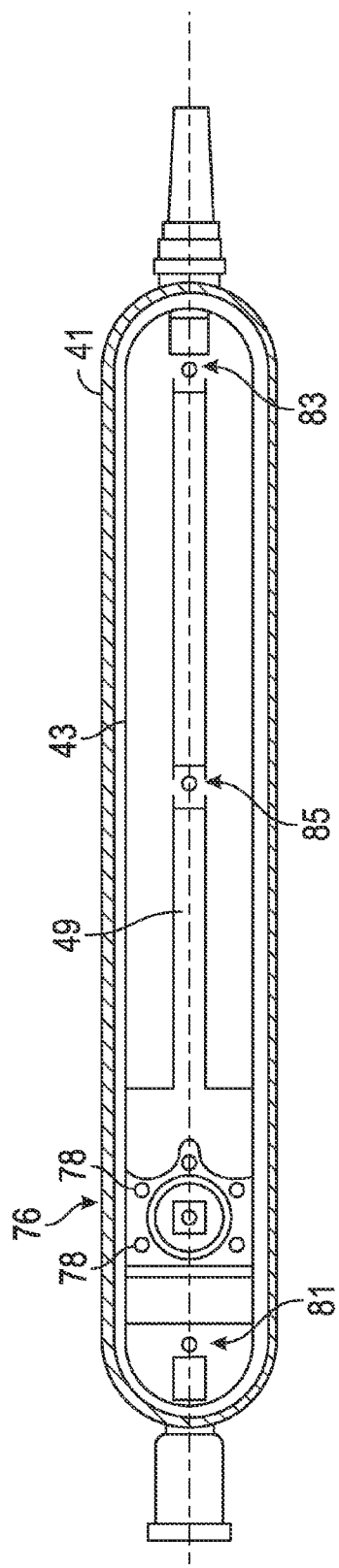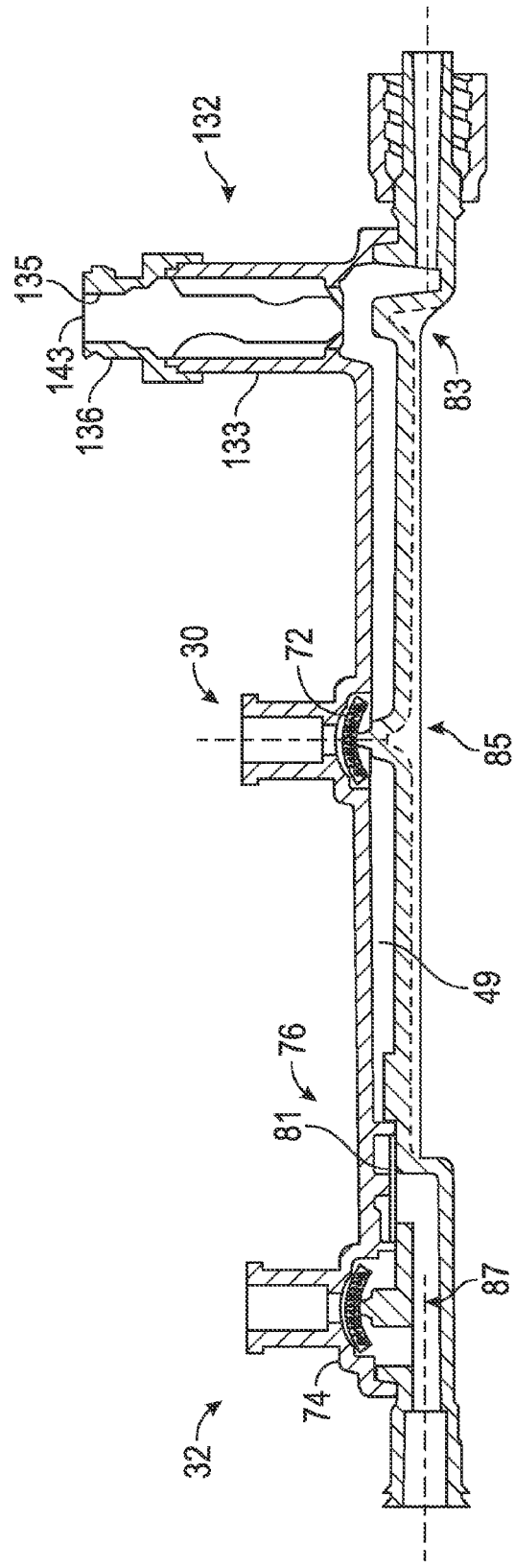

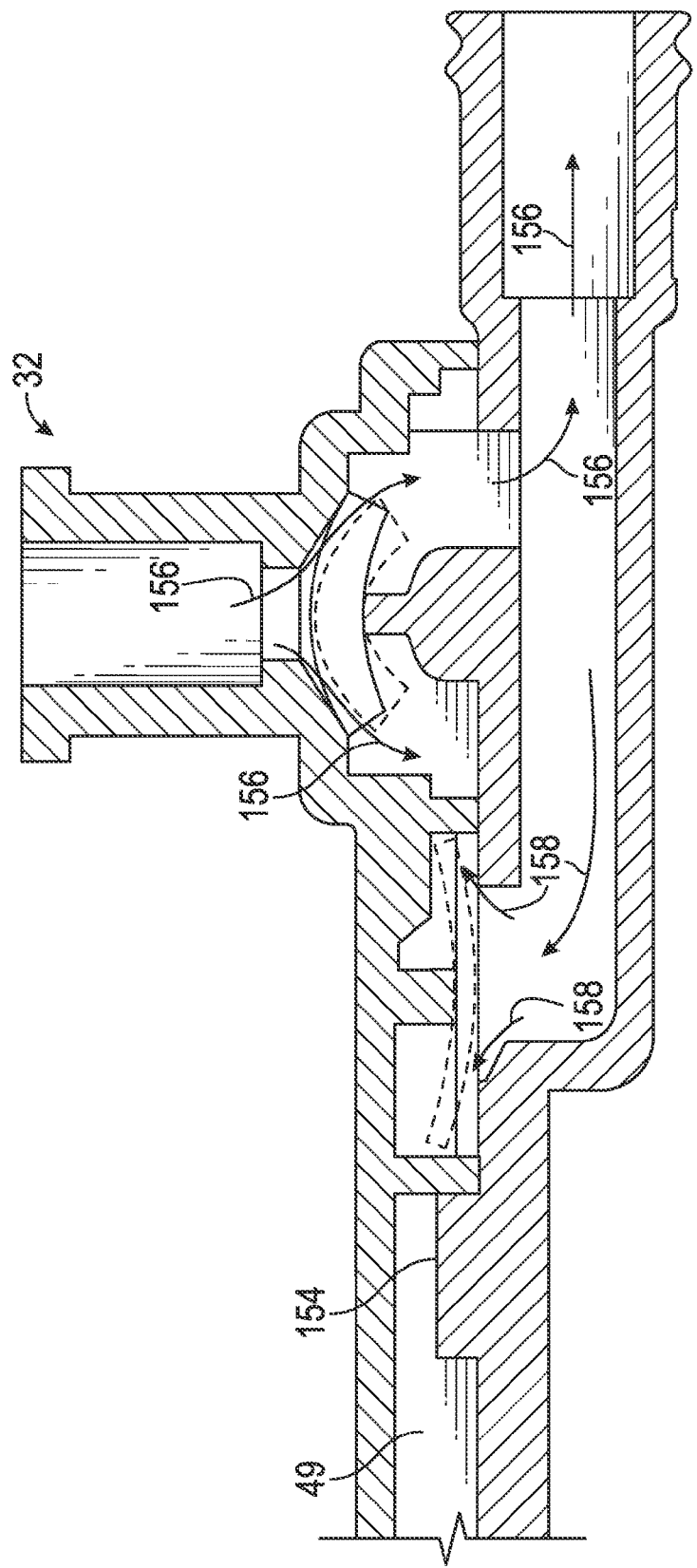

MULTI-VALVE INJECTION/ASPIRATION MANIFOLD WITH NEEDLELESS ACCESS CONNECTION

This application is a Continuation of application Ser. No. 13/564,669, filed Aug. 1, 2012, which is a Continuation of application Ser. No. 10/816,183, filed Mar. 31, 2004, issued as U.S. Pat. No. 8,257,320 on Sep. 4, 2012, which is a Division of Ser. No. 10/113,087, filed Apr. 1, 2002 and now abandoned, which is a Continuation-in-Part of application Ser. No. 09/154,939, filed Sep. 17, 1998 and now issued as U.S. Pat. No. 6,364,861 on Apr. 2, 2002, which are all hereby incorporated by reference in their entireties.

BACKGROUND OF THE INVENTION

1. Field of the Invention

This invention relates generally to ports for injecting fluids into an intravenous (IV) line, and more specifically to injection manifolds including multiple injection ports.

2. Discussion of the Prior Art

Patients are commonly injected with IV solutions which are initially provided in a bottle or bag and dripped into the vein of the patient through an IV line. Typically an injection port is provided along the line and adapted to function with a syringe to permit an injectate to be added to the IV solution. If a large quantity of injectate, or multiple injectates, are to be added to the IV solution, multiple ports may be required. In such a case, an injection manifold can be disposed in the IV line to provide multiple injection ports.

A check valve is also commonly included in the IV line where it is disposed upstream from the injection manifold. It is the purpose of the check valve to permit fluid flow only in the direction of the patient. This ensures that the injectate flows downstream toward the patient, not upstream toward the IV reservoir.

The prior art is deficient in that it does not adequately provide for check valves at locations than upstream of the ports. Doing so has its advantages in certain applications in which the prior art falls short.

In the past, IV manifolds have been provided with an elongate and generally flat configuration in order to facilitate use of the multiple injection ports. The flow channel through the manifold has also had this elongate wide configuration, and consequently, has been susceptible to the formation of air pockets, and to generally uneven flow characteristics. In the vicinity of the injection ports, the manifolds of the past have also developed dead spaces where the injectate has tended to collect rather than mix with the IV solution. Other IV manifolds have been provided with a round tube defining the flow channel. Injection ports have been connected to this tube at a "T" junction. In this case, the flow channel has remained separate and the problems with dead spaces in the ports have been significant.

Injection ports of the past have generally included only valves with a single valve seal. These seals have not been capable of withstanding high pressure such as those sometimes associated with an injection into an adjacent port. The resulting high back pressure has sometimes caused the valve element to deform and lodge in the lumen of the port, rendering the port inoperative.

In the past, the ports associated with injection manifold have not been provided with characteristics permitting the aspiration of fluids from the flow channel. This is sometimes desirable in order to remove air from the manifold or withdraw a blood sample. In these cases, a separate aspiration port has been required in addition to the injection manifold.

Even the three valve seat system provided by the embodiment having an apertured valve element of the instant invention has some drawbacks for certain applications. For example, this embodiment requires relatively high pressure for both aspiration and injection.

Some injection ports have been provided with operative cages which mechanically open the valves. In this case a syringe having a male Luer fitting is relied on to push the cage against the valve element in order to open the valve. Due to wide tolerance variations in the plastic parts associated with the syringes, the male Luer fittings can sometimes extend into the injection port a distance greater than that required to open the valve. In many of these cases, damage to the injection port has resulted.

Although the cage and valve element embodiment of the instant invention provides a means for permitting unimpeded aspiration, and although the cage of the instant invention provides for inserting a variety of male Luers without damaging the port or manifold, the cage adds a separate piece and increases the complexity of the overall device. With the cage embodiment, changes are also required in the port itself to accommodate the cage. For example, a large portion of the second seat must be removed in order to provide room for the cage.

SUMMARY OF THE INVENTION

These problems with the injection ports and manifolds of the prior art are overcome with the present invention which provides for a generally U-shaped flow channel that extends axially of the manifold. By restricting the IV solution to this flow channel, the flow characteristics through the manifold are greatly enhanced. Importantly, there are no dead spots in the fluid flow through the manifold. Furthermore, the flow of fluid can be directed against the valve element of the injection port to avoid dead spots around the valve. A check valve can be included in this manifold and disposed at one end of the elongate housing. An infusion/aspiration port is preferably disposed upstream of the other injection ports and downstream of the check valve.

Alternatively, the check valve may be located between an upstream injection/aspiration port and a downstream injection/aspiration port. In this way an injection/aspiration port may be advantageously located upstream of the check valve. As can be understood by those skilled in the art, locating the check valve downstream of at least one of the injection/aspiration ports enables either pulling IV fluid from the IV line into a syringe or reservoir of the port upstream of the check valve without pulling fluid from downstream of the check valve, or pulling of injectate from the at least one port into the IV line upstream of the manifold.

A preferred injection port is provided with two seals, a line seal and a surface seal, which provide for low pressure and high pressure operation, respectively. When an injectate is being introduced into an adjacent port, the resulting high back pressure is resisted by the high pressure surface seal of the port.

In an injection port embodiment including a cage, the cage can be configured to be axially compressible. These compressible characteristics accommodate the wide tolerance variations in the plastic parts which sometimes tend to cause a male Luer fitting to extend into the injection port a distance greater than that necessary to open the associated valve. By providing the cage with these compressible characteristics, the tolerance variations are accommodated without damaging the valve element.

Alternatively, and perhaps preferably, a needleless access connection (NAC) can be included in the manifold. The NAC has the advantage of enabling the aspiration as well as the injection of fluids therethrough. This feature is achieved with a simple and reliable structure. In operation, a male Luer is inserted into a aperture of the NAC in order to open a NAC valve and permit aspiration or injection of fluids through the NAC. As can be appreciated, the aspiration and injection through the NAC requires very low pressures.

In one aspect, the invention includes an injection port adapted for use with an IV line. The port includes a housing defining a flow channel and having an injection lumen. First portions of the housing define a first valve seat, while second portions of the housing define a second valve seat. A valve element, disposed to extend transverse to the injection lumen has properties for forming a first seal with the first valve seat at a first pressure, and a second seal with the second valve seat at a second pressure greater than the first pressure. The first valve seat, which forms part of the second valve seat, has the shape of a continuous line, while the second valve seat has the shape of a continuous surface.

In another aspect, the invention includes a port for injecting an injectate into a flow channel for aspirating a fluid from the flow channel. The port includes a housing defining the flow channel and having a lumen disposed in fluid communication with the flow channel. First portions of the housing define a first valve seat while second portions of the housing define a second valve seat. A valve element has properties for forming a first seal with the first valve seat and a second seal with the second valve seat when the valve element is in a natural state. The valve element has properties for opening the first seal in response to a positive pressure in the lumen to facilitate flow of an injectate into the flow channel. The valve element also has properties for opening the second seal in response to a negative pressure in the lumen in order to facilitate flow of the fluid from the flow channel into the lumen of the port. The first valve seat is formed on the side of the valve element opposite the flow channel. The second valve seat is formed on the side of valve element opposite the first valve seat. This embodiment may include a post with the second seal being formed around the post.

In an additional aspect of the invention an injection manifold includes a first body member and second body member forming a housing. First portions of the housing define a flow channel adapted to receive an IV solution flowing in an IV line. Second portions of the housing define at least one port with an injection lumen, the port having a outside diameter. The first portions of the housing have a width greater than the outside diameter of the port and define the flow channel with a width less than the diameter of the port. The flow channel will typically have a U-shaped configuration.

In a further aspect of the invention an injection/aspiration port includes a housing with first portions defining a flow channel and second portions defining an injection/aspiration lumen. Third portions of the housing define a valve seat around the lumen. A valve element is biased toward the injection/aspiration lumen and forms a seal with the valve seat. A valve cage is disposed in the lumen and adapted to be moved by insertion of a male Luer fitting into the lumen against the valve element to open the seal and permit two-way flow between the lumen and the flow channel. The valve cage is axially compressible to accommodate slight variations in the size of the male Luer fitting.

These and other features and advantages of the present invention will be more apparent with a description of preferred embodiments and reference to the associated drawings.

DESCRIPTION OF THE DRAWINGS

FIG. 5 is a side elevation view of the manifolds illustrated in FIGS. 2A-4D;

FIG. 6 is a top plan view of the manifolds illustrated in FIG. 5;

FIG. 7A is a cross-section view taken along lines 7-7 of FIG. 5;

FIG. 7B is a cross-section view taken along lines 7-7 of FIG. 5 and explicitly incorporating the NAC and the check valve, with the check valve disposed between two of injection ports;

FIG. 8A is an axially cross-section view taken along lines 8-8 of FIG. 6;

FIG. 8B is an axial cross-section view taken along lines 8-8 of FIG. 6 and explicitly showing the NAC and the check valve, with the check valve disposed between two of the injection ports;

FIG. 14 is a cross-section view similar to FIG. 12 and showing a further embodiment of the invention with a valve in a normal state;

FIG. 15 is a cross-section view similar to FIG. 14 and illustrating the valve in an injection state;

FIG. 16 is a cross-section view similar to FIG. 14 and illustrating the valve in an aspiration state;

FIG. 17 is a cross-section view similar to FIG. 12 and showing the valve in a normal sealed state;

FIG. 18 is a cross-section view similar to FIG. 17 illustrating the cage in a compressed configuration with the valve in an injection/aspiration state; and FIG. 19 is a section view of an end of the manifold of the second and third alternative embodiment similar to FIG. 8B.

DESCRIPTION OF THE PREFERRED EMBODIMENTS AND BEST MODE OF THE INVENTION

Figure 1:
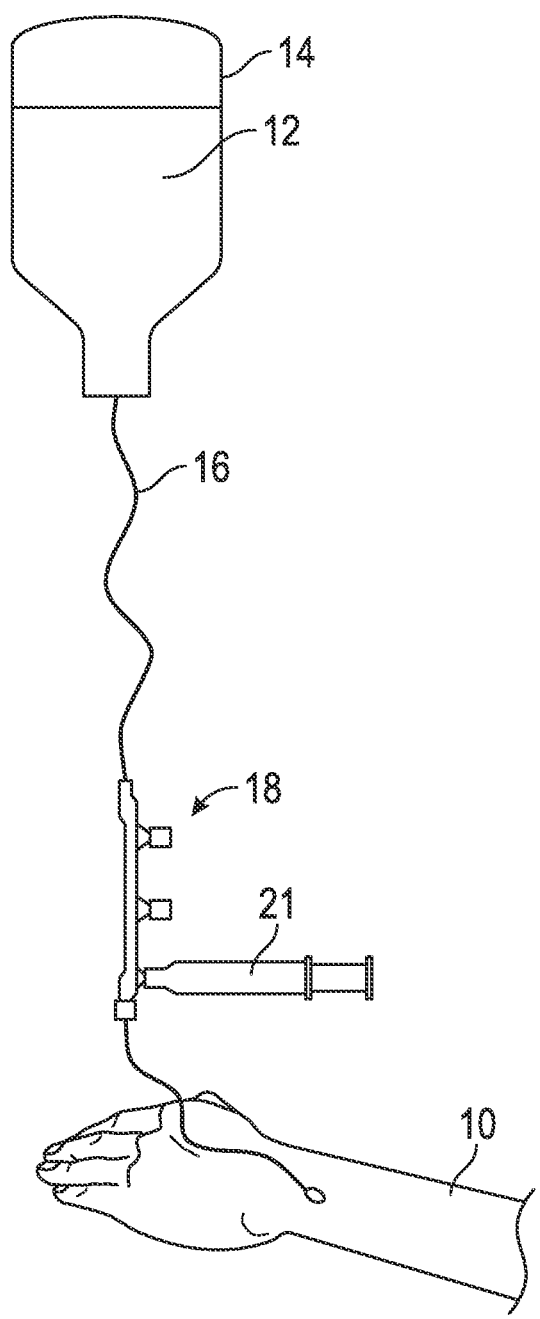
FIG. 1 is a perspective view of an arm of a patient with an IV solution appropriately administered through an injection manifold of the present invention.

The arm and hand of a patient are illustrated in FIG. 1 and designated generally by the reference numeral 10. An IV solution 12 contained in a reservoir, such as a bottle or bag 14, is appropriately communicated to the patient 10 through an IV line 16. An injection manifold 18 of the present invention is connected in series with the line 16 and provides a site where drugs and other fluids can be injected, typically through a syringe 21, into the IV solution in the line 16.

Figure 2A:
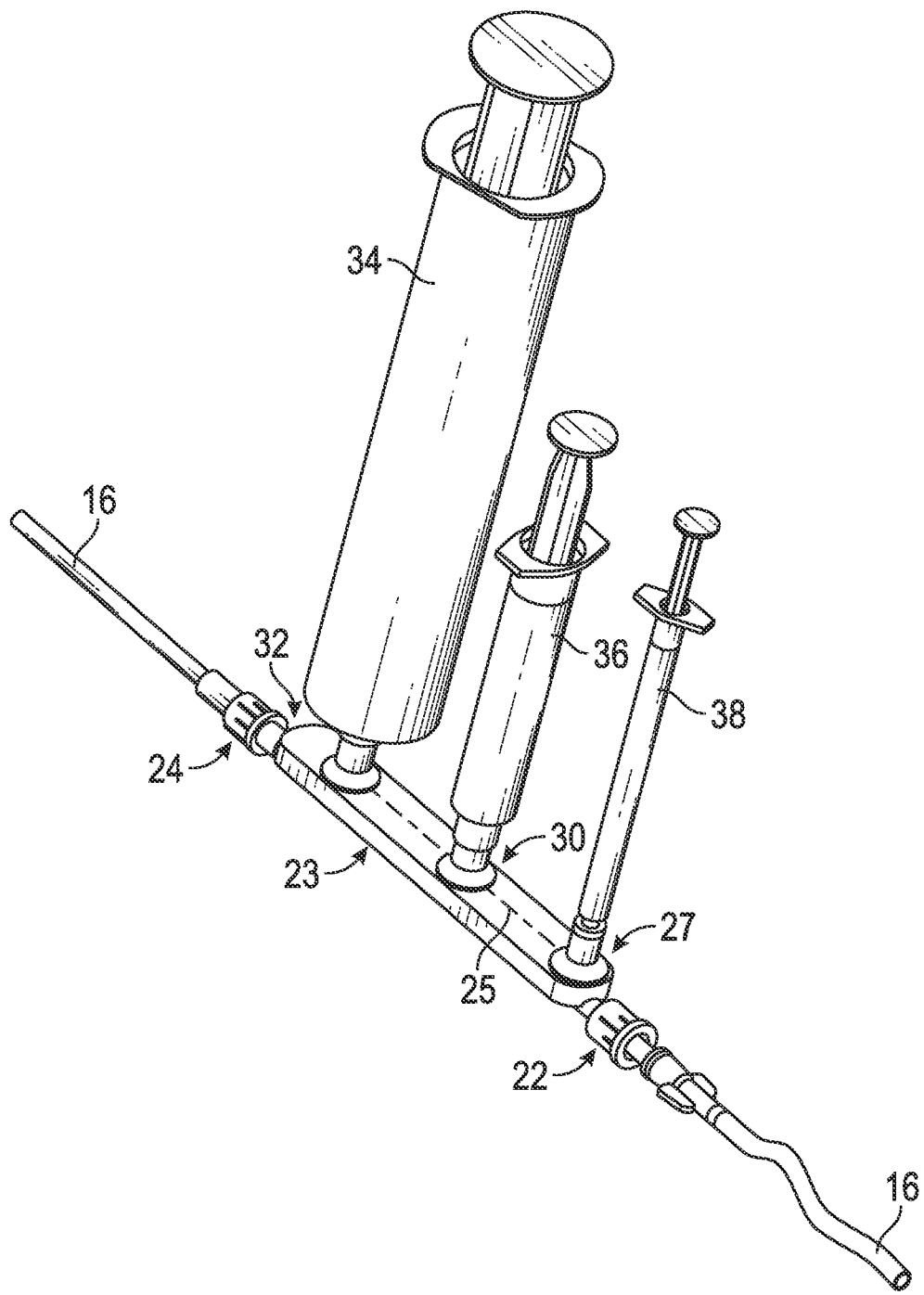
FIG. 2A is a perspective view of the manifold having three injection ports and syringes of various sizes connected to the ports.

The manifold 18 of a preferred embodiment is illustrated in greater detail in FIG. 2. In this view it can be seen that the manifold 18 has a housing 23 with an elongate configuration, and extends generally along an axis 25. The housing 23 is connected in series with the IV line 16, for example by a pair of connectors 22 and 24, so that the flow channel and the IV line 16 also extends through the housing 23.

A plurality of injection ports 27, 30 and 32 can be molded integrally with the housing 23 and spaced along the length of the housing 23. In FIG. 2, a 60 mm syringe 34 is connected to the port 32, while a 10 mm syringe 36 and a 5 mm syringe 38 are connected to the ports 30 and 27, respectively. There will of course be situations requiring three syringes such as the 60 cc syringe 34 that must be coupled to the manifold 18 at the same time. This will require that the ports 27, 30 and 32 be spaced sufficiently that the ports 27 and 32 are separated by a distance equal to two times the diameter of the 60 cc syringe 34, and the center port 30 disposed intermediate with the outer ports 27 and 32.

Figure 3A:
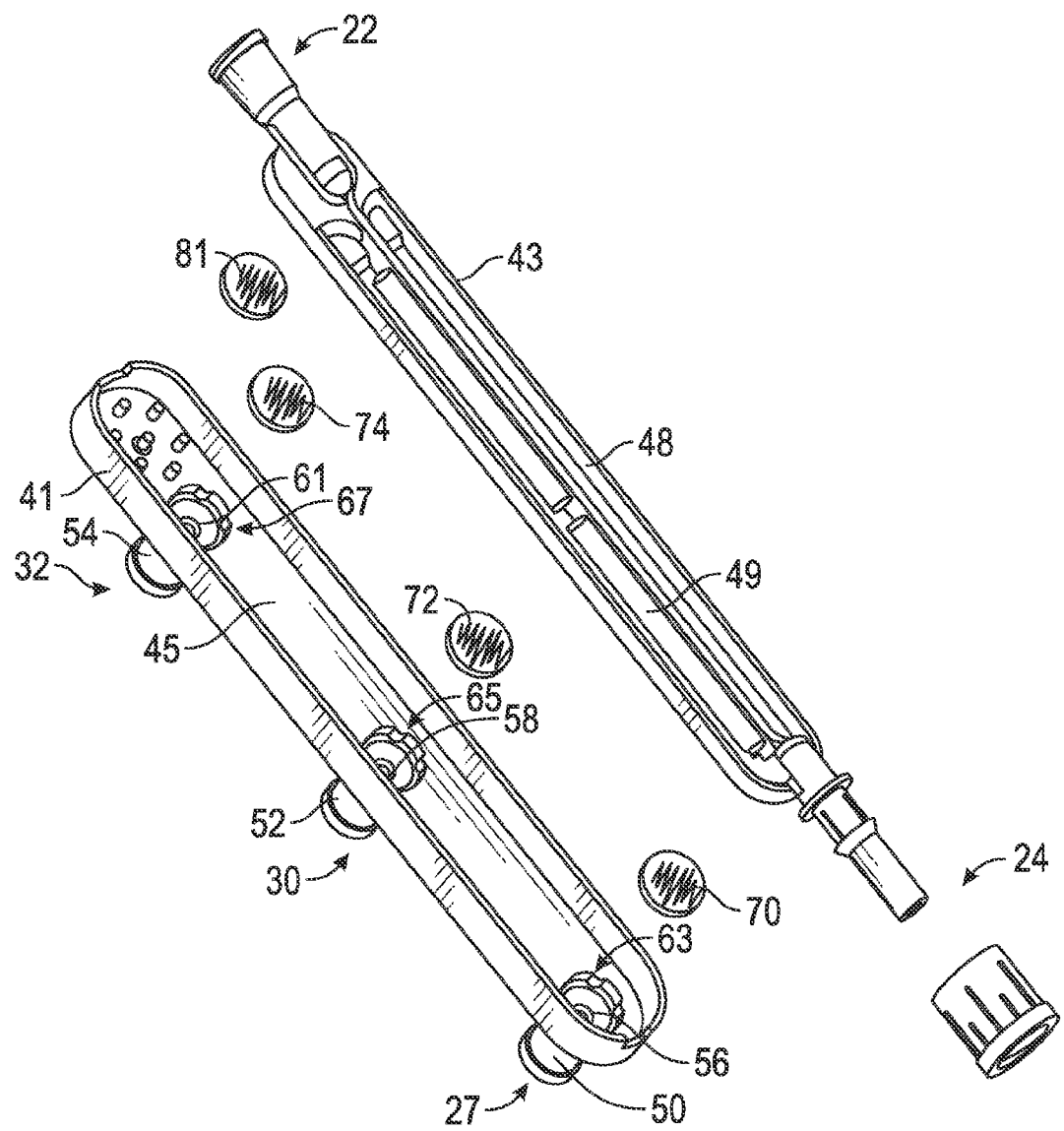
FIG. 3A is an exploded view of the manifold of FIG. 2A illustrating first and second members forming a housing, and showing the interior of the first member and the exterior of the second member.

The manifold 18 is further illustrated in the exploded views of FIGS. 3 and 4. In these views, the housing of a preferred embodiment is illustrated to include a first housing member 41 and a second housing member 43. The first housing member 41 has in inner side 45 illustrated in FIG. 3 and an outer side 47 illustrated in FIG. 4. Similarly, the second housing member 43 has an inner side 46 and an outer side 48. From these views it can be seen that each of ports 27, 30 and 32 includes a cylinder 50, 52 and 54, respectively, which projects from the outer surface 47 of the first housing member 41. These cylinders 50, 52 and 54 in turn define lumen 56, 58 and 61, respectively, which are in fluid communication with the flow channel 49. The cylinders 50, 52 and 54 also form with the first housing member 41 a plurality of cavities 63, 65 and 67, respectively, which are adapted to receive associated valve elements 70, 72 and 74. The operation of these ports 27, 30 and 32 will be discussed in greater detail below.

In this particular embodiment, a check valve 76 is provided at one end of the manifold 18. In this case, the check valve 76 is formed with a plurality of pins 78 which extend from the inner side 45 in a generally circular configuration. These pins 78 are adapted to receive a valve element 81. The manifold 18 is intended to be connected in the IV line 16 and oriented with the check valve 76 connected to the upstream side of the line 16.

Figure 11:
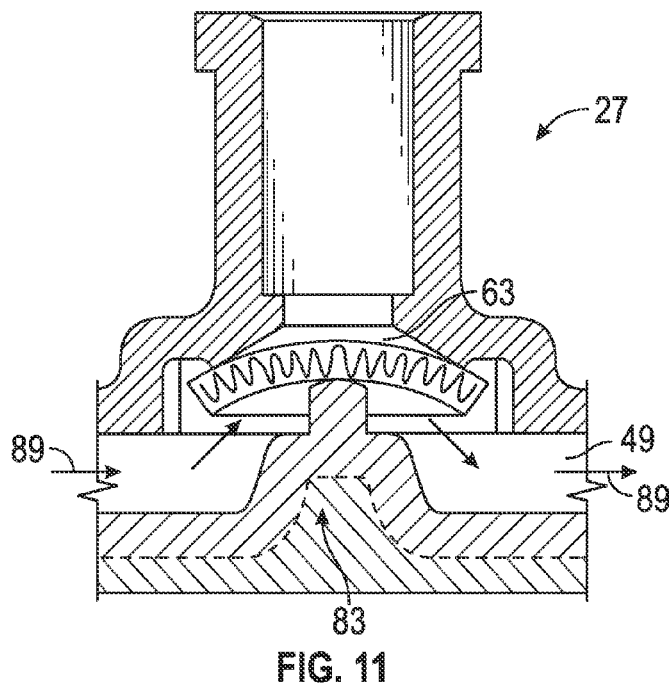
FIG. 11 is a radial cross-section view of an injection port taken along lines 11-11 of FIG. 6.

Perhaps best illustrated in FIG. 4 are a plurality of protrusions 83, 85 and 87 which interrupt the flow channel 49 at each of the associated ports 27, 30 and 32, respectively. These protrusions 83, 85 and 87, which are also illustrated in the assembled view of FIG. 7 and the cross-section view of FIG. 8, are of particular advantage to the present invention as they disrupt the flow of the IV solution 12 along the channel 49 and direct that flow into the associated cavities 63. With this directed fluid flow, the cavities 63, 65 and 67, and particularly the valve elements 70, 72 and 74, are constantly washed so that there are substantially no dead spots associated with the injection ports 27, 30 and 32. In the past, these dead spots have been particularly common in the concave area beneath the valve 70, 72 and 74. With the fluid flow directed specifically onto the concave side of each element 70, 72 and 74, the dead spots are greatly minimized. This diverted flow is illustrated in greater detail in FIG. 11 where the cavity 63 and valve element 70 of the injection port 27 are washed by the IV solution flow which is illustrated by arrows 89.

In relation to this washing effect, FIGS. 7A-8B illustrate how the valve cavities associated with ports 27, 30 and 32 have a height less than each of a width and a length. In this way, a flow path is formed such that a liquid passing through the manifold, readily impinges on an underside of the valve elements in the cavities. Thus the structural relationship of height to width and length reduces stagnation. Flow is further enhanced by structural details in the cavities. Specifically, the portion of the cavities forming valve the valve seats and the valve elements 70, 72, 74 themselves form a concave surface on a side of the valve elements 70, 72, 74 opposite to the valve seats.

Figure 9:
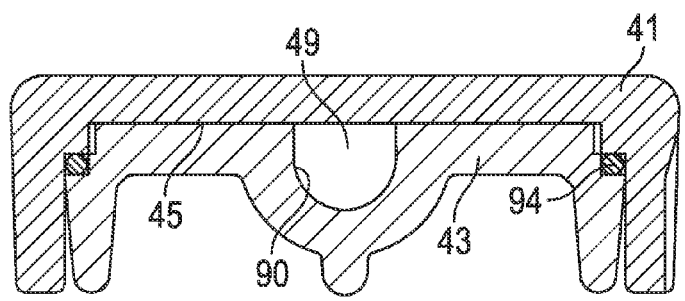
FIG. 9 is a cross-section view taken along lines 9-9 of FIG. 6.

With reference to FIG. 9, it can be seen that a preferred embodiment of the manifold 18 provides a flow channel 49 with a U-shaped configuration. This shape is generated by providing the inner surface 45 of the first housing member 41 with a generally planar configuration. When the second housing member 43 is mated to the first housing member 41, a U-shaped cavity 90 in the surface 48 automatically provides the flow channel 49 with the U-shape desired. In this particular embodiment, the generally planar inner surface of the housing member 41 makes it possible to also provide the outer surface 47 with a planar configuration. This shape greatly facilitates wiping the manifold 18 between the adjacent ports 27 and 30, and the ports 30 and 32.

Figure 10:
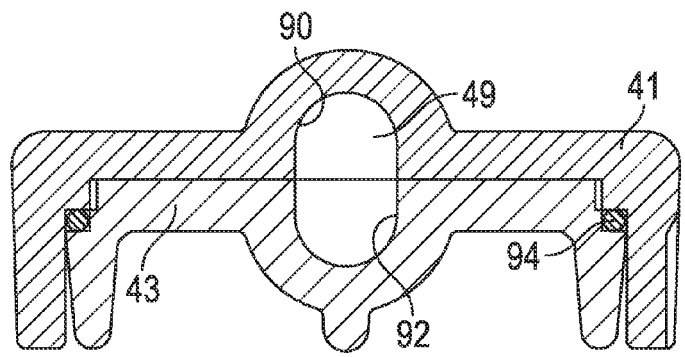
FIG. 10 is a cross-section view similar to FIG. 9 and illustrating a further embodiment of the manifold.

In an alternative embodiment illustrated in FIG. 10, the flow channel 49 is defined by the U-shaped cavity 90 formed in the first housing member 41, and by a second U-shaped cavity 92 formed in the second housing member 43. When these parts are joined, the two cavities 90 and 92 provide the flow channel 49 with the shape of an oval. The views presented by FIGS. 9 and 10 also are best suited to illustrate the mating relationship of the first housing member 41 and the second housing member 43. These members 41 and 43 are operatively positioned with their respective surfaces 45 and 46 in close proximity so that these-surfaces do not form any part of the flow channel 49. This contributes greatly to the flow characteristics within the channel 49 and avoids many of the air pockets and dead spots associated with the full-width flow channels of the prior art. The second housing member 43 can be fixed to the first housing member 41 in this operative position by means of adhesive or by heat seals 94.

Figure 12:
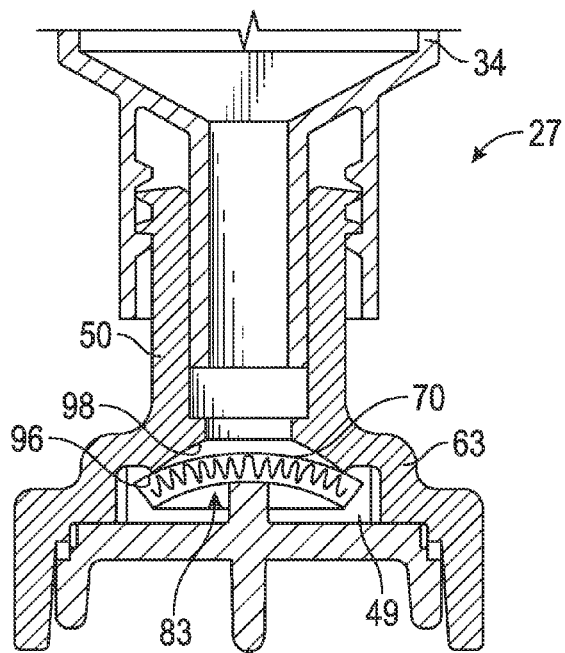
FIG. 12 is a radial cross-section view of the injection port taken along lines 12-12 of FIG. 6.
Figure 13:
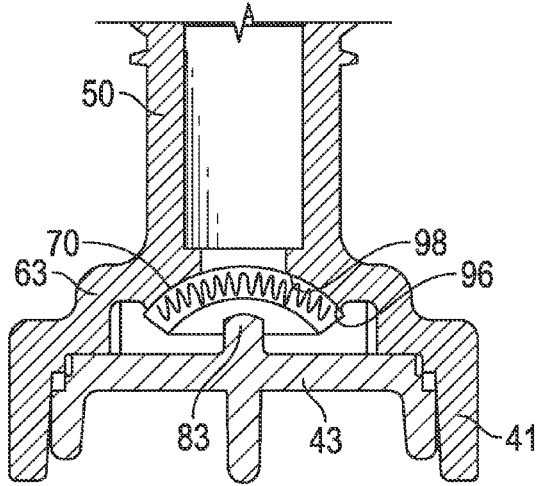
FIG. 13 is a cross-section view illustrating the port of FIG. 12 in a high pressure configuration.

Operation of the injection port 27 is best described with reference to FIGS. 12 and 13. In these views, it will be noted that the port 27 includes portions 96 which define a first valve seat and portions 98 which define a second valve seat. The first valve seat 96 forms a slight annulus above the valve element 70. In its normal configuration, the valve element 70, which has elastomeric properties, is biased by the protrusion 83 beneath the element 70 to form a seal with the first valve seat 96.

When an injectate is introduced through one of the adjacent ports, such as port 30 or 32, a relatively high pressure occurs in the flow channel 49. By operation of the check valve 76, this pressure is exerted against the underside of the valve element 70 of the port 27. In the manifold 18, the higher pressure will cause the valve element 70 to deform as illustrated in FIG. 13 until it comes into contact with the second valve seat 98 as illustrated in FIG. 13. With this second valve seat 98 providing surface contact with the valve element 70, a high pressure seal is formed without radical deformation or damage to the valve element 70.

Under some circumstances, it is desirable to have an injection port, such as the port 32, function not only to receive injectate into the flow channel 49, but also to aspirate or withdraw fluid from the flow channel 49. When an injection/aspiration port, such as the port 32, is included in the manifold 18, it is preferably disposed on the upstream side of the other ports so that injectate introduced in the other ports is not aspirated from the manifold 18. Since the check valve 76 is also to be positioned upstream of the ports 27-32, it is desirable that the injection/aspiration port 32 be positioned next to the check valve 76.

Figure 14:
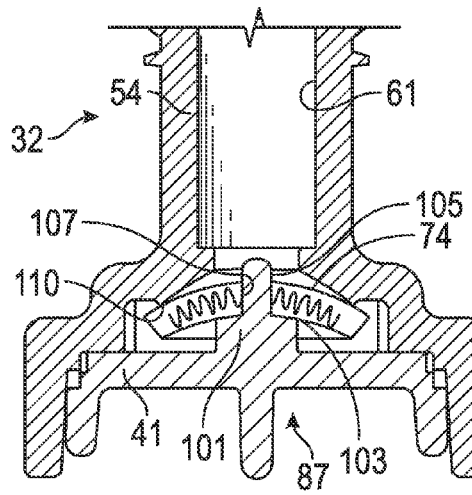
FIG. 14-16 are cross-section views similar to FIG. 12 illustrating operation of an injection port which also has aspiration characteristics.
Figure 15:
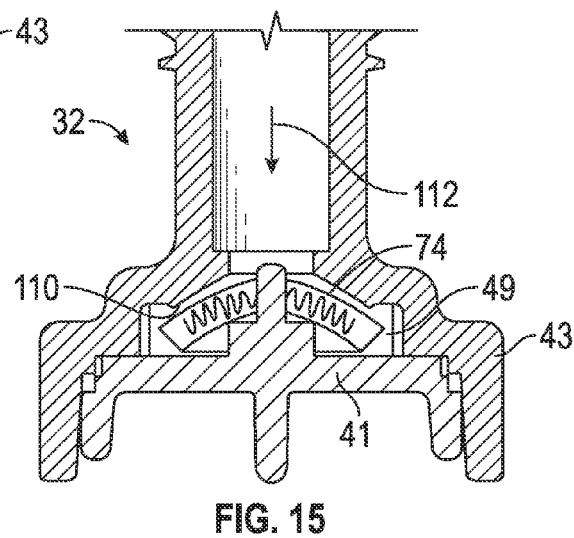
Figure 16:
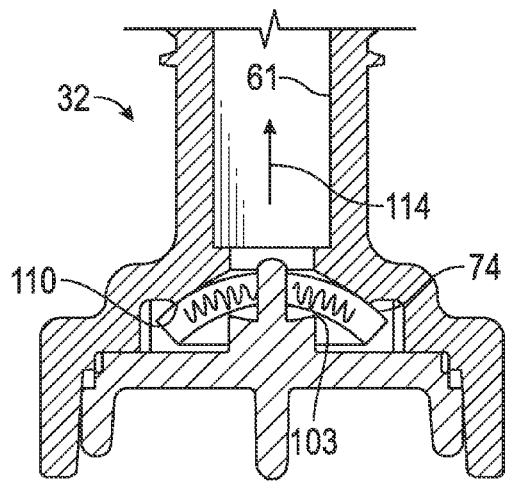

A preferred configuration for the injection/aspiration port 32 is illustrated in FIGS. 14-16. In this embodiment, the projection 87 is configured with a shoulder 101 which forms a third valve seat 103, and a post extending toward the lumen 61 of the port 32. In this case, the valve element 74 is provided with a central aperture or hole 107 which is sized to receive the post 105. In the manner previously discussed with reference to the FIG. 12 embodiment, a first valve seat 110 can be formed above the valve elements 74 with the third valve seat 103 formed beneath the valve element 74. In its normal state, the port 32 is positioned with the valve element 74 biased to form a first seal with the first valve seat 110 and a second seal with a third valve seat 103 as illustrated in FIG. 14. Under the fluid pressure of an injectate, as illustrated by an arrow 112 in FIG. 15, the valve element 74 is bent downwardly opening the first seal at the first valve seat 110. The second seal with the valve seat 103 is strengthened by this downward pressure against the valve element 74. Nevertheless, the injectate 112 flows through the first valve and into the flow channel 49.

Aspiration is accommodated by applying a suction to the lumen 61 as illustrated by an arrow 114 in FIG. 16. This causes the valve element 74 to raise off of the shoulder 103 which form the second valve seat. Fluid within the flow channel 49 is thereby permitted to pass between the valve element 74 and the post 105 into the lumen 61. In all cases, the hole 107 in the valve element 74, and the post 105, maintain the valve element 74 centered with respect to the valve seats 110 and 103, respectively.

Figure 18:
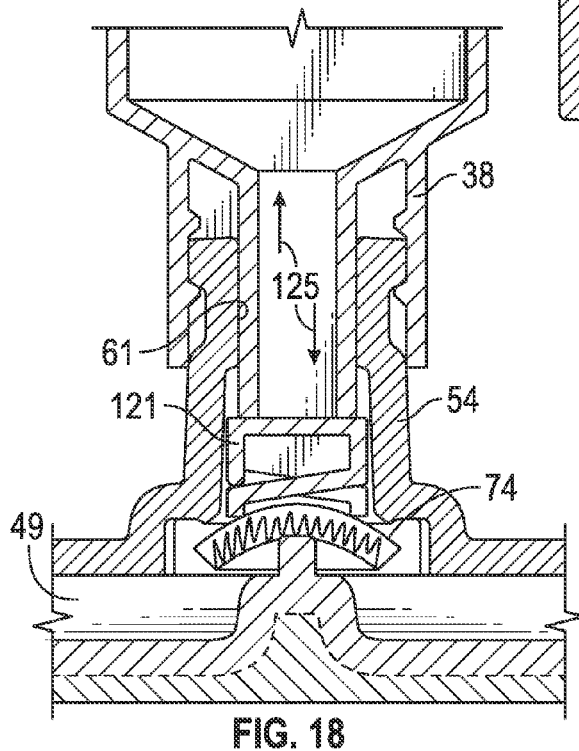
FIGS. 17 and 18 are cross-section views similar to FIG. 12 and illustrating a further embodiment including a mechanical cage for actuating the valve element.
Figure 17:
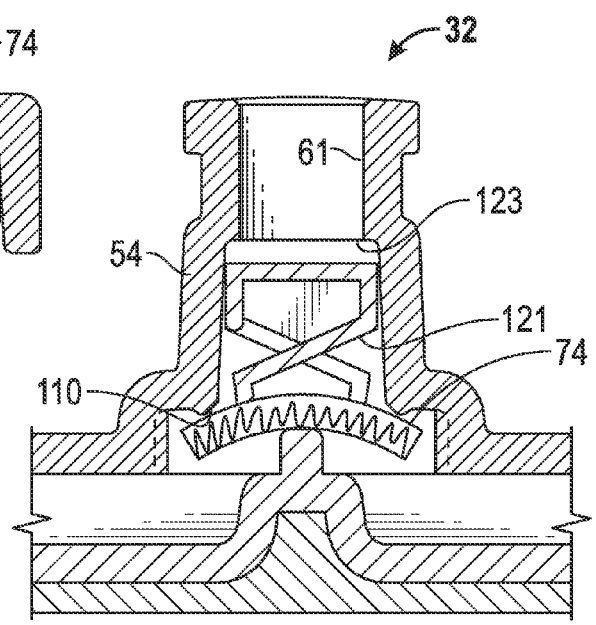

A further embodiment of the injection/aspiration port 32 is illustrated in FIGS. 17 and 18. In this case, the port 32 is operated not by fluid pressure, but rather mechanically by the force of the syringe 38 acting upon a cage 121. In this case, the cylinder 54 defining the lumen 61 is provided with an interior shoulder which faces downwardly and prevents the cage 121 from moving upwardly within the lumen 61. In this embodiment, the cage 121 fits between the shoulder 123 of the cylinder 54 and the upper surface of the valve element 74. The cage 121 can be formed of wire or other resilient material and provided with a configuration which is axially compressible. The advantage of this port 32 is that it does not rely upon fluid pressure to open, but rather the mechanical force of a male Luer fitting 123 associated with the syringe 38.

With the tolerances accommodated in forming the Luer fitting 123 and in forming the lumen 61, it can be appreciated that the syringe 38 can extend a variable distance into the cylinder 54. If the cage 121 is provided only as a rigid element, damage to the valve element 74 can result when the male Luer fitting 123 extends too far into the lumen 61. In the illustrated embodiment, wherein the cage 121 is axially compressible, this great variation in distance of insertion can be accommodated by the cage 121 so that the valve element 74 is not radically deformed. When the valve element 74 is opened by the cage 121, two-way flow through the port 32 can be accommodated as illustrated by the arrows 125 in FIG. 18. Thus, the valve element 74 is separated from the valve seat 110 opening the valve to either receive injectate into the flow channel 49 or remove fluid from the flow channel 49.

Figure 2B:
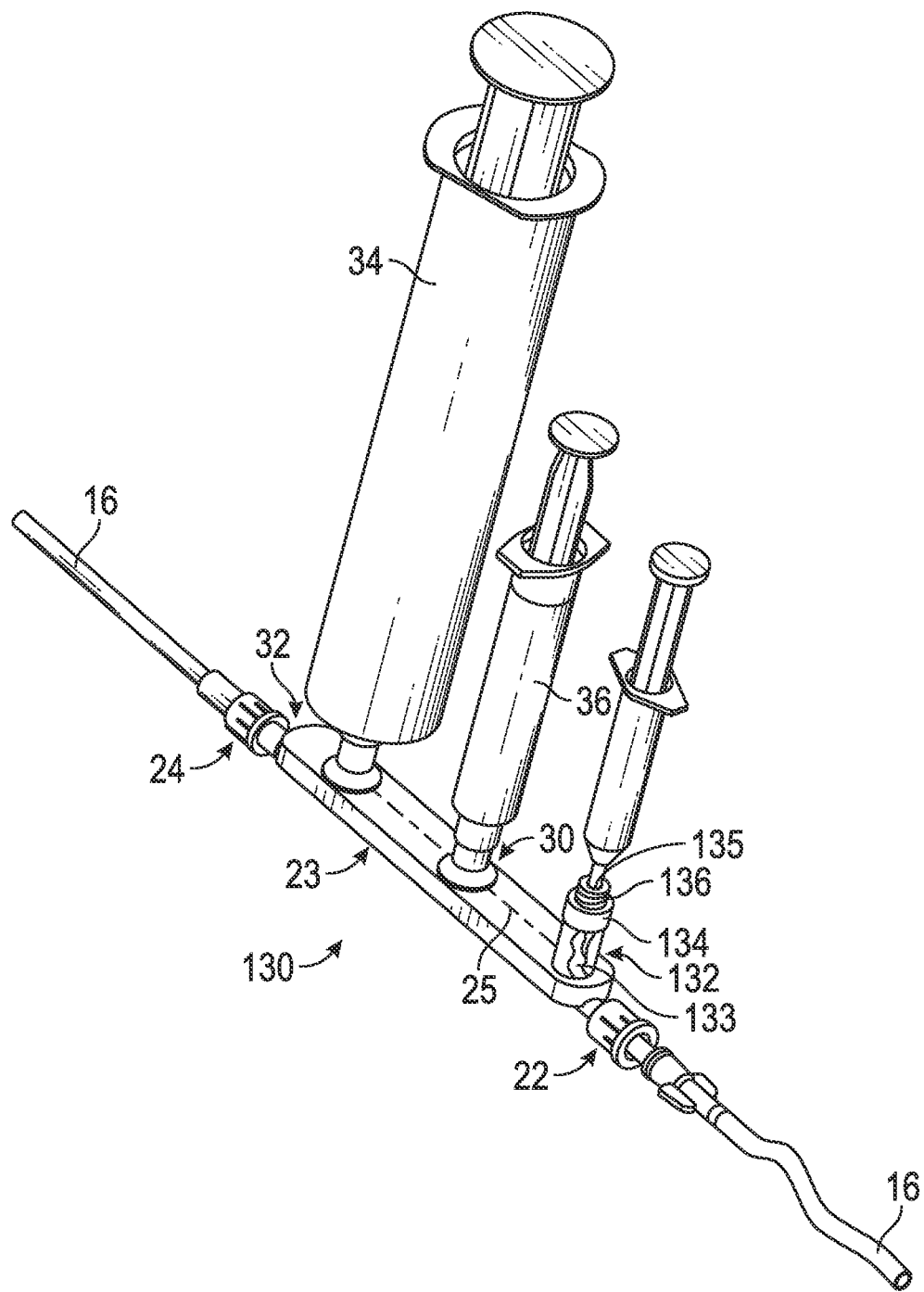
FIG. 2B is a perspective view of an additional embodiment of the manifold having two injection ports and a NAC and syringes of various sizes connected to the port and NAC.

FIG. 2B illustrates a modified manifold 130. The modified manifold 130 differs from the embodiment of FIG. 2A in that a port 27 has been replaced by a needleless access connection (NAC) 132. All other aspects of the manifold remain the same. However, the NAC has several details that are unique and important. The NAC is made up of a body portion 133 having a top piece 134 thereon. The top piece has an aperture 135 therethrough forming part of a conduit through the NAC body 133. The top piece 134 is also provided with a fastening means 136. A bottom end 137 of the NAC 132 is connected to the housing 23. In this embodiment, the NAC can be rigidly connected to or formed integrally with the housing 23.

Figure 3B:
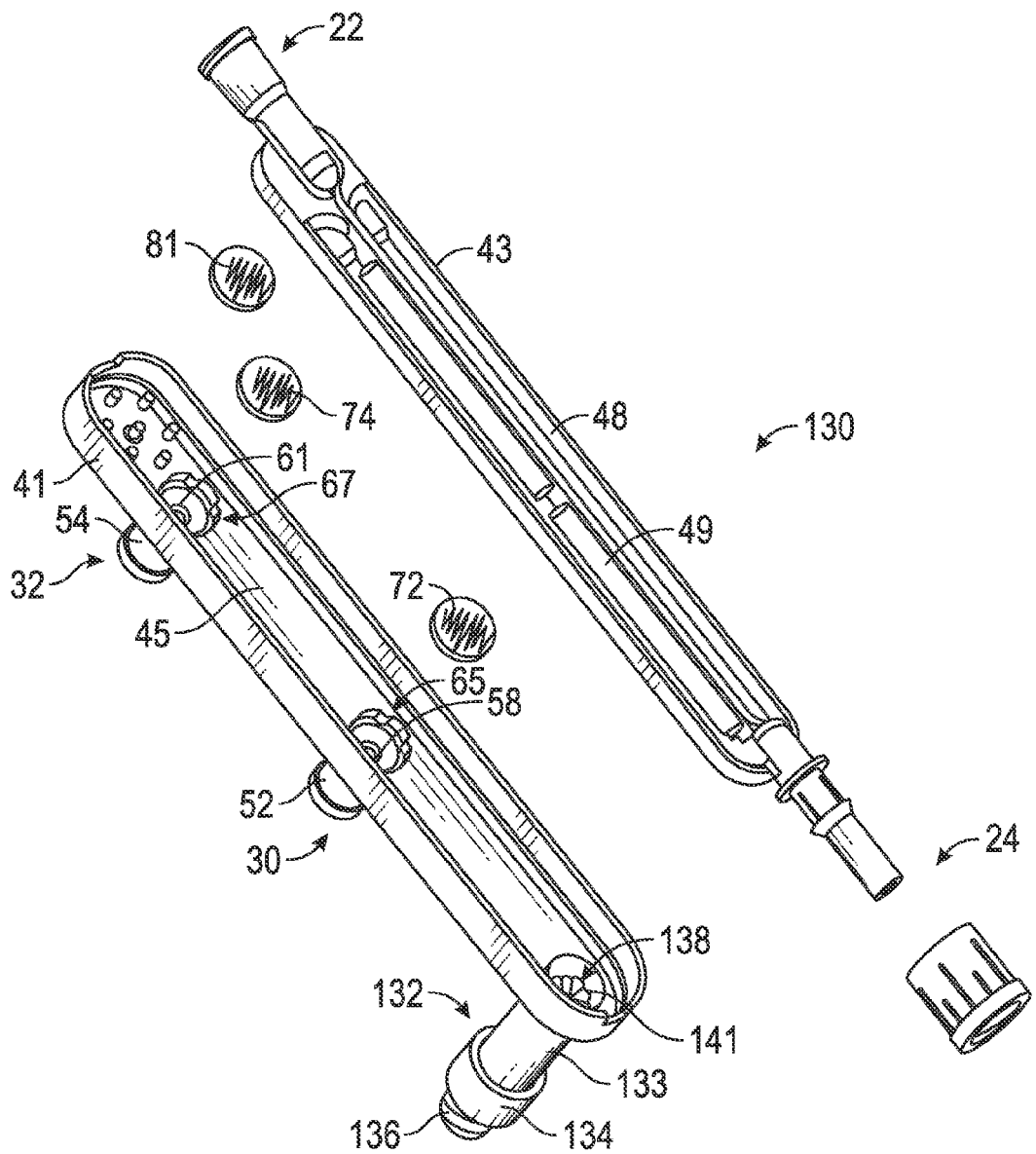
FIG. 3B is an exploded view of the embodiment of FIG. 2B including the NAC.

FIG. 3B perhaps best illustrates an aspect of the NAC bottom end 137. This aspect is a grate 138 integrally formed with the bottom end 137. Grate 138 provides an opening 141 through which fluid may flow. At the same time, grate 138 retains an elongate valve element 143 within the NAC 132. The elongate valve element is further retained by a shoulder 144 formed on the interior of top piece 134. In this way, the elongate valve element 143 is captured in the NAC 132 and extends between the grate 138 and the top piece 134.

Figure 4A:
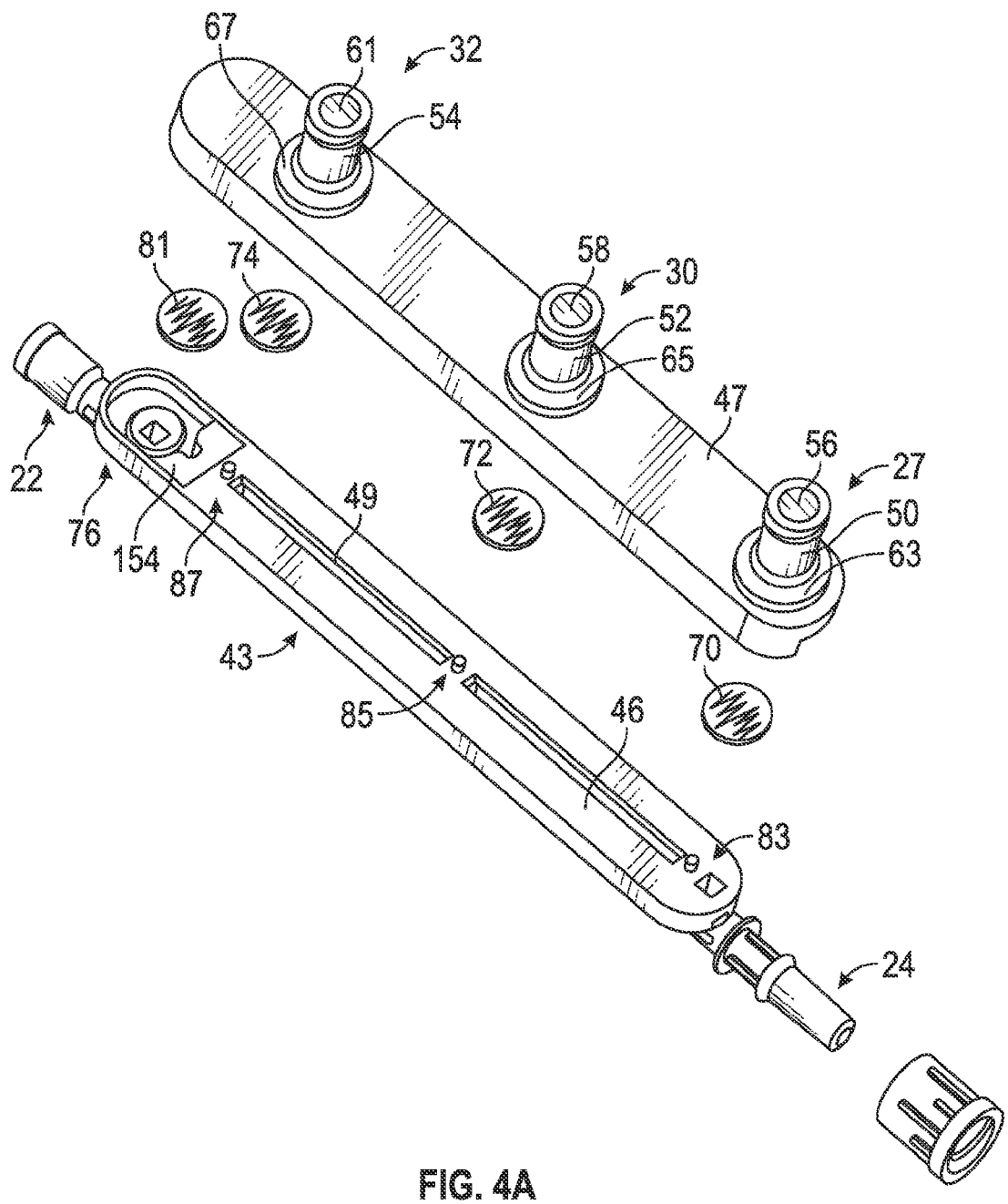
FIG. 4A is an exploded view similar to FIG. 3A but showing the interior of the second member and the exterior of the first member.
Figure 4B:
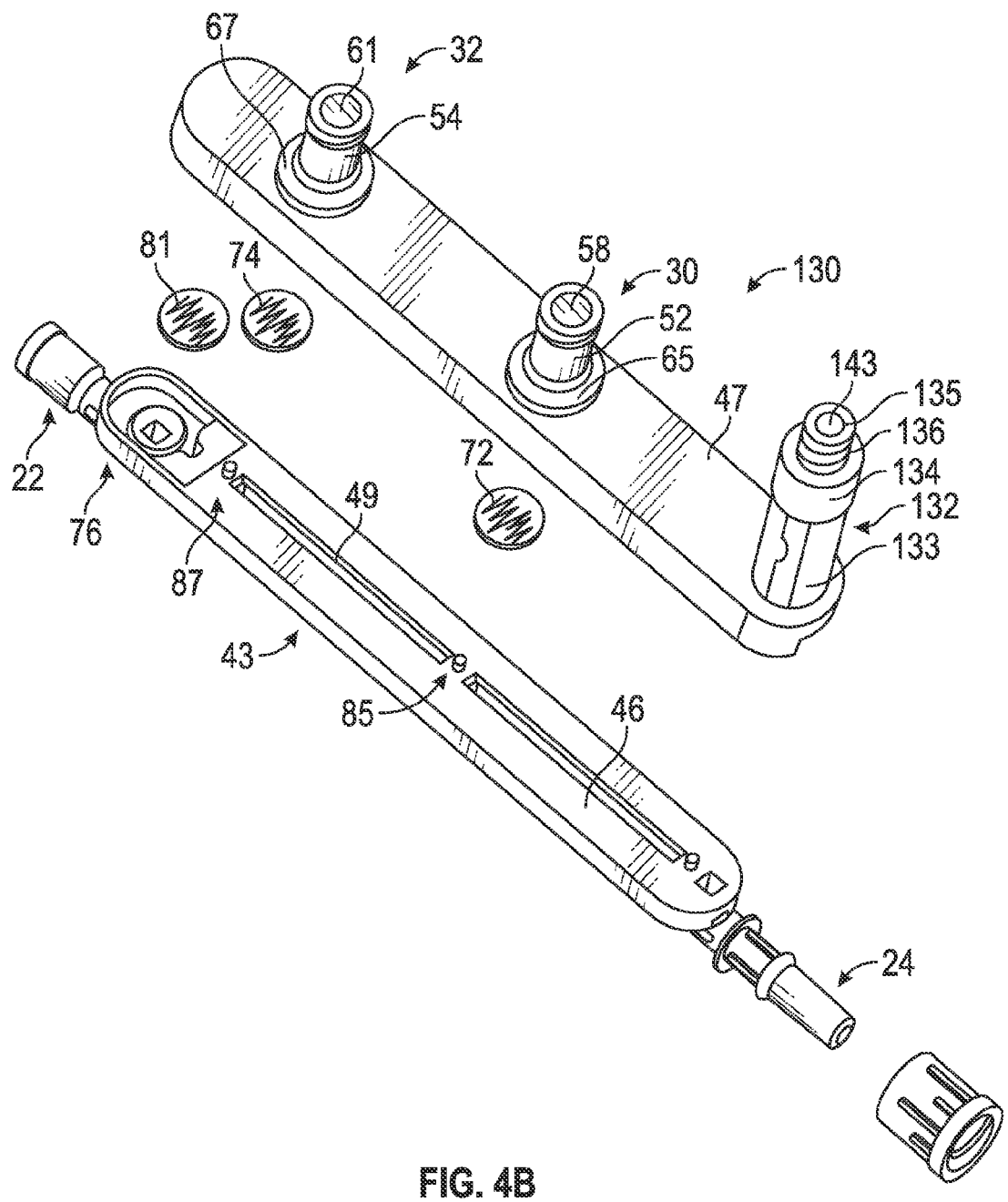
FIG. 4B is an exploded view similar to FIG. 4A of the embodiment of FIG. 3B including the NAC.
Figure 4C:
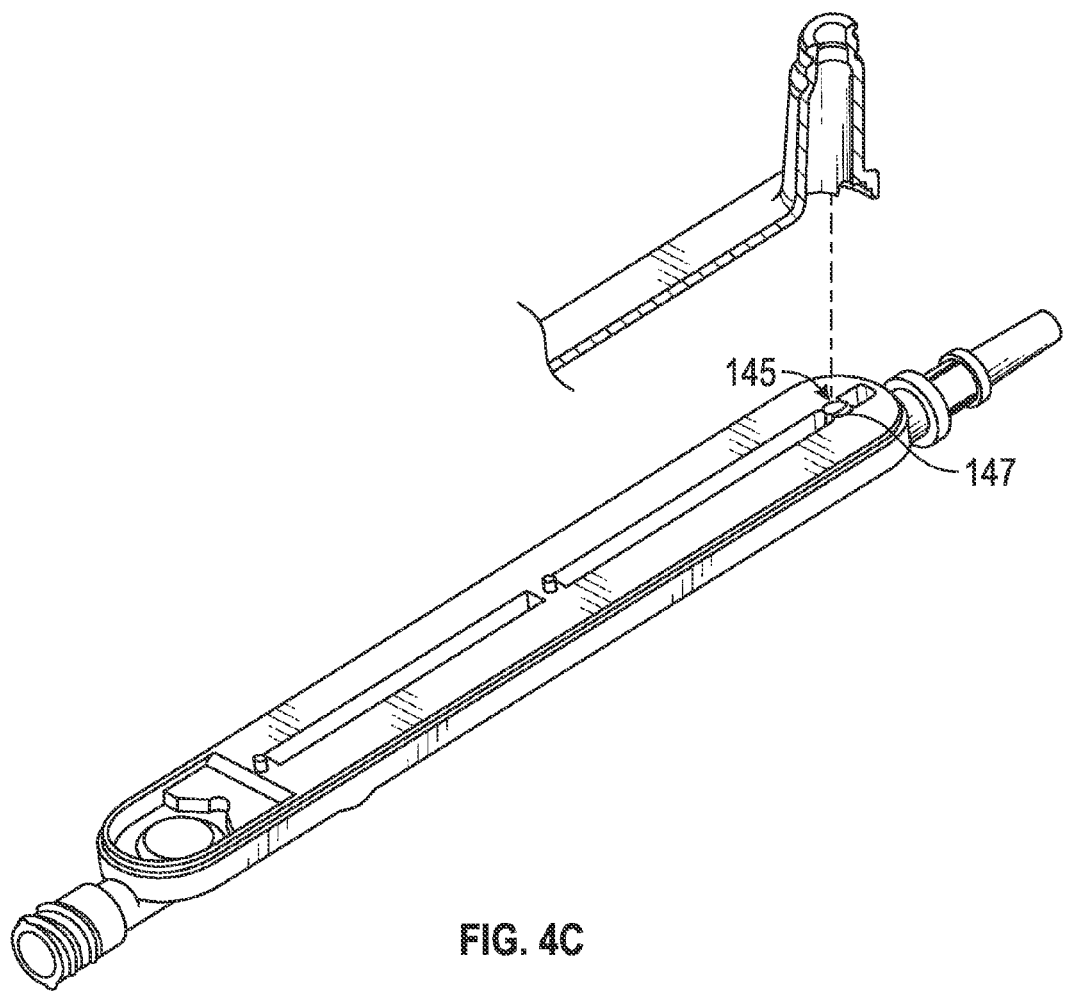
FIG. 4C is an exploded view similar to FIG. 4B of the embodiment of FIG. 3C.
Figure 4D:
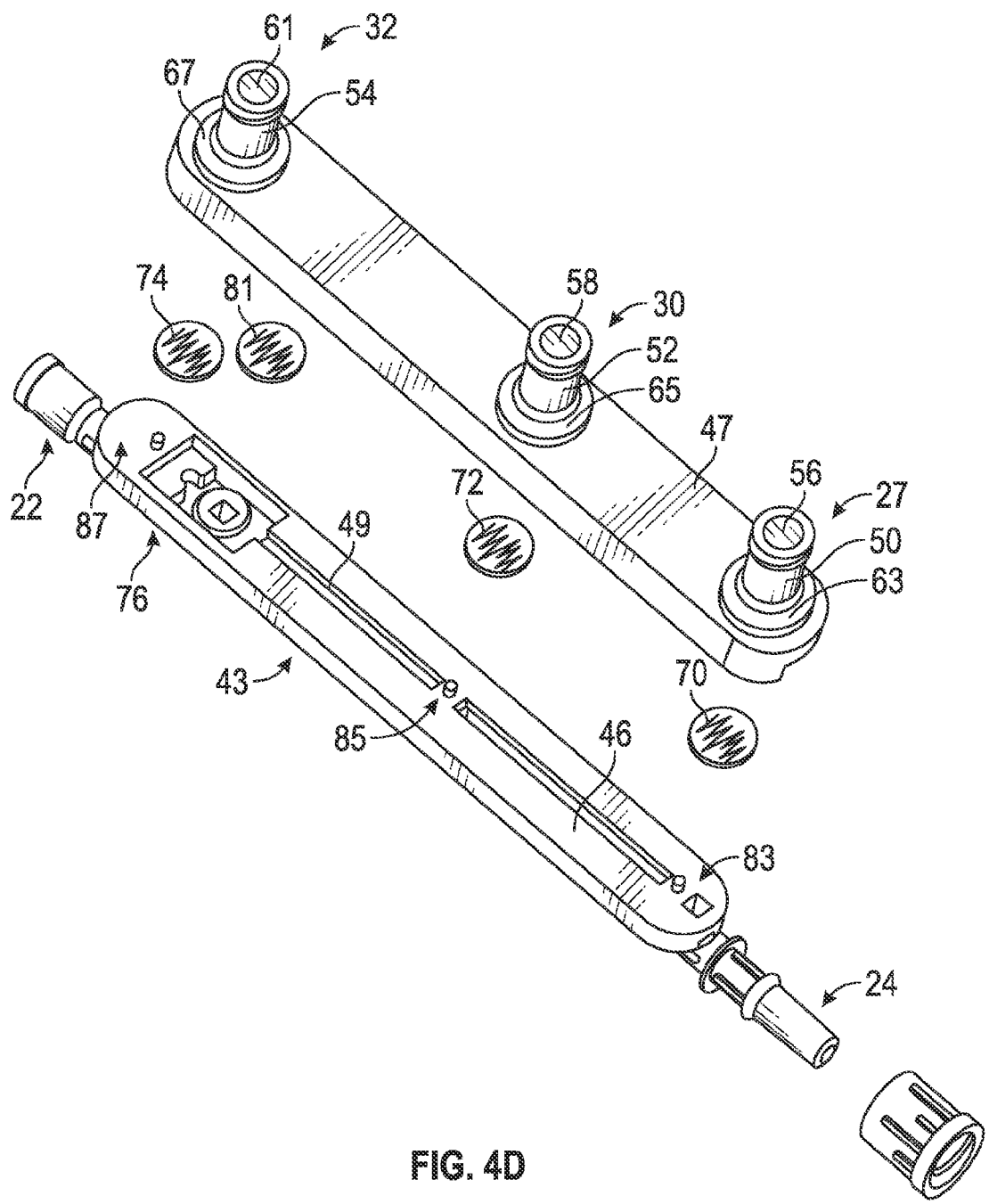
FIG. 4D is an exploded perspective view of the embodiment of FIG. 3C with the check valve disposed between two ports.

As can be seen from FIG. 4C, the grate 138 may be replaced by a grate means 145. In this embodiment the grate means 145 is not formed integrally with the NAC body portion 133. Rather the grate means 145 is formed separately as a part of housing member 43. In this way, it can be appreciated that the elongate valve element 143 will be captured in the NAC 132 when the housing members 41 and 43 are assembled together. Importantly, grate means 145 still provides an opening at a bottom end of the NAC 132. This opening is provided by slot 147 and other structure that permits fluid to flow in and out of a bottom end 137 of NAC 132.

As can be seen in the Figures, the NAC has a diameter of width greater than the other injection valves, yet narrower than the housing of the manifold 132. The bottom end 137 of the NAC 132 is rigidly connected to the manifold housing. Furthermore, the bottom end 137 of the NAC 132 has an opening for placing the conduit or interior of the NAC 132 in fluid communication with the flow channel 49 of the manifold 132.

Figure 3C:
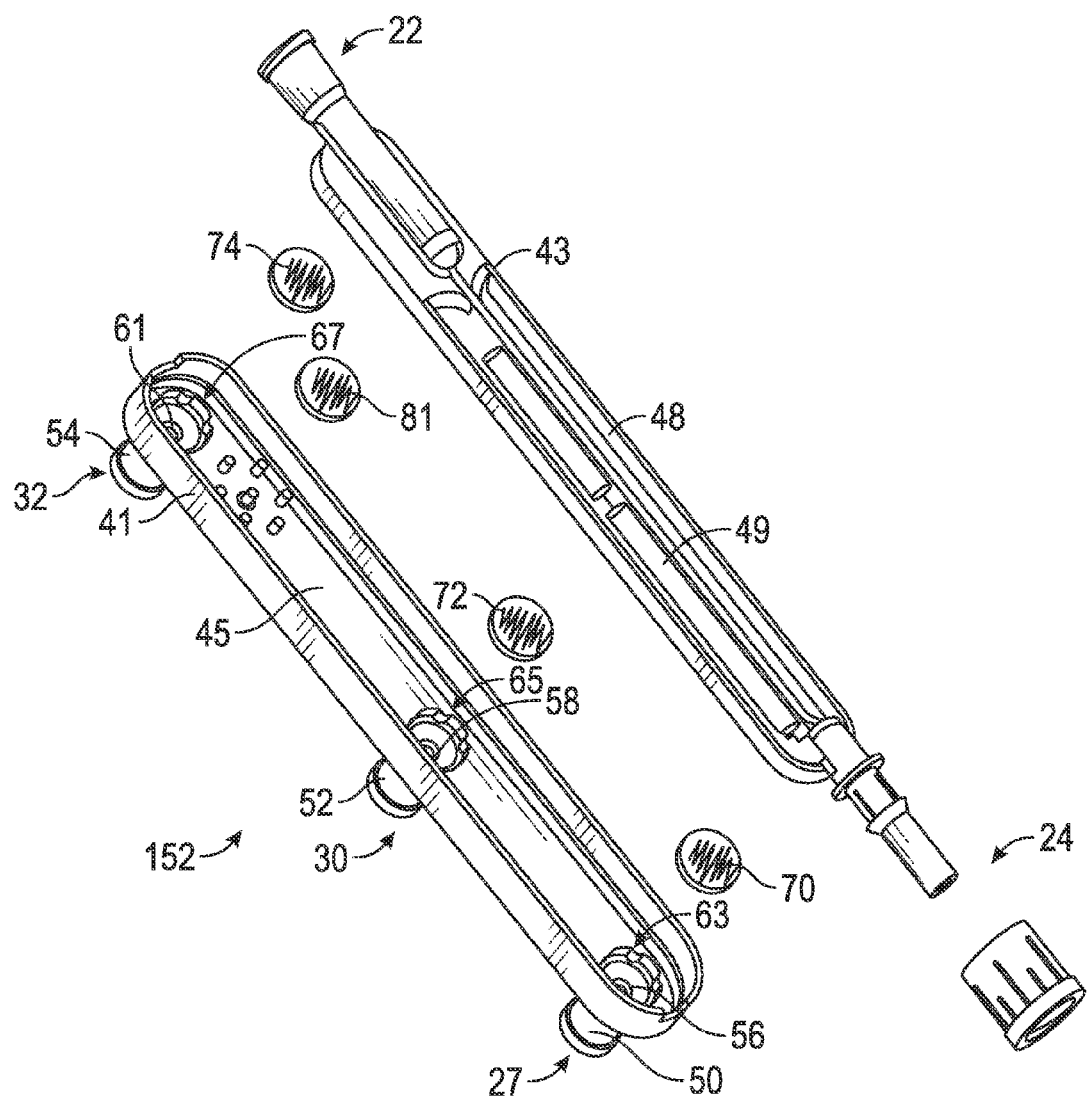
FIG. 3C is an exploded view of a further embodiment similar to FIG. 3A with the check valve disposed between two of the ports.

A second alternative embodiment or modified manifold 152 is perhaps best illustrated in FIG. 3C. The second modified manifold 152 is different from the manifold 18 in that the locations of the injection port 32 and the check valve 76 have been interchanged. All other aspects remain substantially the same. However, additional flow channel 154 best illustrated in FIG. 4A and FIG. 19 have a different and significant relationship to other elements of the invention in this embodiment. The additional flow channel 154 of the previously described embodiments normally defines a flow between an IV fluid inlet and a first port 32. However, in the second modified manifold 152 the additional flow channel 154 now defines a flow path for the IV fluid between the injection port 32 and flow channel 49. In this case additional flow channel 154 is in direct fluid communication with flow channel 49.

FIG. 19 illustrates how the second modified manifold advantageously functions. As shown, injection flow through port 32 and indicated by arrows 156 can be caused by a net negative pressure in the upstream portion of the IV line. Of course, if the net negative pressure is in a downstream portion of the IV line relative to the check valve 76, then flow 156 will move through the check valve 76 and downstream. However, as can be appreciated, by manipulating the pressure upstream of the manifold in the IV line between a negative net pressure and a positive net pressure, the flow may be alternated between an injection flow 156 and a downstream through flow 158. By thus cycling negative and positive pressures upstream in the IV line, a repeated draw of fluid from a reservoir connected to port 32 and a forcing through of the fluid through the manifold may be achieved. Of course, a single cycle or a half cycle may be implemented as well.

A third alternative embodiment or alternatively modified manifold 165 is depicted in FIG. 5. As shown in dashed lines the manifold of this embodiment incorporates the NAC 132 in place of port 27 and interchanged locations of injection port 32 and the check valve 76. All other aspects of the manifold are substantially the same.

FIG. 7B is a sectional view along lines 7-7 of FIG. 5 and explicitly showing the third alternatively modified manifold 165. Likewise, FIG. 8B is a sectional view taken along lines 8-8 of FIG. 6 and also shows the third alternatively modified manifold 165.

FIG. 8B best illustrates the elongate valve element 143 of the first and third alternative embodiments. The elongate valve element 143 has a plug 170 at its upper end and an elastomeric shaft 172 extending downwardly and engaging the grate 138. As can be appreciated, the elastomeric shaft resiliently biases the plug 170 into the aperture 135 of the NAC 132.

In use, when a male Luer is forced into the aperture 135 of the NAC and seals the NAC against fluid passage or reflux in and out of the top of the NAC. The plug 170 is resiliently displaced downwardly into the NAC 132. The elastomeric shaft 172 cants and permits this displacement, and fluid communication is thereby established between the Luer tip and the NAC. The elastomeric shaft 172 may include structural features that enhance canting such as, for example, recesses in the elastomeric shaft 172. It can also be appreciated that the height of the NAC and the resiliency of the elongate valve element 143 accommodate a wide range of male Luer lengths without harming or adversely affecting the manifold.

The NAC of the instant invention has an advantage over many of the injection ports described above in that the NAC may be used for aspiration as well as for injection of fluids therethrough. Furthermore, the NAC is capable of operating at lower pressures. For example, the NAC may be operated at pressures of 1.5 psi or less depending on other relative pressures in the system. On the other hand the injection ports of the previously described embodiments operate at higher pressures. That is, for example, in the range of 2-6 psi. As can be appreciated by those skilled in the art the NAC therefore can be appropriately used to inject fluids therethrough from an IV bottle or bag source.

It will be appreciated that many variations of these embodiments will now be apparent to those skilled in the art. Certainly, the configuration of the flow channel 49 can be varied widely to accommodate and improve fluid flow through the manifold 18. Also, the shape of the projections 83, 85 and 87 can be varied considerably as long as the fluid flow is directed into the cavities containing the valve elements. Other embodiments providing multiple valve seats to accommodate high and low pressures will also be apparent. In addition, other ports facilitating aspiration from the flow channel 49 will also be apparent to either provide two-way fluid communication or alternatively to otherwise direct the fluid flow as illustrated in the Figures.

Based on these and many other variations which will now be apparent, one is cautioned not to determine the extent of the concept only with reference to the disclosed and illustrated embodiments, but rather to determine the scope of the invention only with reference to the following claims.

What is claimed is:

1. A manifold adapted for use with an intravenous line, comprising:
a housing comprising a first port, a second port, and a flow channel between the first and second ports;
a first check valve disposed within the flow channel proximate the first port and configured to prevent flow in the flow channel to travel past the first check valve in a direction from the second port toward the first port;
at least one access port coupled to the housing between the first check valve and the second port, the access port in fluid communication with the flow channel;
a cavity between the at least one access port and the flow channel, wherein a first valve seat is formed by a cavity surface adjacent to the access port;
a protrusion disposed in the flow channel at the at least one access port such that a fluid in the flow channel is directed toward the cavity; and
a valve element disposed in the cavity between the first valve seat and the protrusion such that a fluid flowing from the first port to the second port contacts an inside surface of the valve element.

2. The manifold of claim 1, wherein the inside surface of the valve element is concave.

3. The manifold of claim 1, wherein a second valve seat is formed by the cavity surface adjacent to the access port.

4. The manifold of claim 1, wherein a third valve seat is formed by the protrusion.

5. The manifold of claim 1, wherein:
when a first intravenous line is coupled to the first port and filled with a fluid, there is a first pressure in the fluid at the first port;
when a second intravenous line is coupled to the second port and filled with a fluid, there is a second pressure in the fluid at the second port;
when a reservoir is coupled to the at least one access port and filled with a fluid, there is a third pressure in the fluid at the at least one access port;
the manifold is configured such that when the first pressure is greater than the second pressure, fluid will flow from the first intravenous line into the second intravenous line and not into the reservoir, and when the first pressure is less than both the second and third pressures, fluid will flow from the reservoir into the second intravenous line and not into the first intravenous line.

6. The manifold of claim 1, wherein the at least one access port comprises a needleless connector configured such that fluid may flow in either direction through the access port when a mating needleless connector is coupled to the access port.

7. The manifold of claim 6, wherein the at least one access port is configured to accept a luer fitting.

8. The manifold of claim 1, wherein the at least one access port is an injection port.

9. The manifold of claim 1, wherein the at least one access port is an aspiration port.

10. The manifold of claim 1, wherein the at least one access port is capable of injection or aspiration.

11. The manifold of claim 1, wherein the flow channel comprises a U-shaped cross-sectional configuration.

12. A intravenous set, comprising:
- a housing comprising a first port, a second port, and a flow channel between the first and second ports;
- a first check valve disposed within the flow channel proximate the first port and configured to prevent flow in the flow channel to travel past the first check valve in a direction from the second port toward the first port;
- at least one access port coupled to the housing between the first check valve and the second port, the access port in fluid communication with the flow channel;
- a first intravenous line coupled at a first end to the first port; and
- a valve element disposed between the at least one access port and the flow channel such that a fluid flowing from the first port to the second port contacts an inside surface of the valve element.

13. The intravenous of claim 12, further comprising a cavity between each access port and the flow channel, wherein a first valve seat is formed by a cavity surface adjacent to the access port.

14. The intravenous of claim 12, further comprising a protrusion disposed in the flow channel at each access port such that a fluid in the flow channel is interrupted and directed toward each cavity.

15. The intravenous of claim 12, further comprising a first fitting coupled to a second end of the first intravenous line and configured to couple to a container that contains an intravenous solution.

16. The intravenous of claim 12, further comprising:
- a second intravenous line coupled at a first end to the second port; and
- a second fitting coupled to a second end of the second intravenous line.

17. The manifold of claim 12, wherein the inside surface of the valve element is concave.

18. The manifold of claim 12, wherein the flow channel comprises a U-shaped cross-sectional configuration.

\* \* \* \* \*